(12) United States Patent
Jakobsson (10) Patent No.: US 11,545,243 B2
(45) Date of Patent: Jan. 3, 2023

(54) MEDICAL DRESSING HAVING IDENTIFIABLE INFORMATION TAG THAT IS ONLY READABLE IF PORTION OF DRESSING IS EXPOSED

(71) Applicant: Mölnlycke Health Care AB, Gothenburg (SE)

(72) Inventor: Conny Jakobsson, Lerum (SE)

(73) Assignee: Mölnlycke Health Care AB, Gothenburg (SE)

(*) Notice: Subject to any disclaimer, the term of this patent is extended or adjusted under 35 U.S.C. 154(b) by 277 days.

(21) Appl. No.: 16/767,204

(22) PCT Filed: Nov. 27, 2018

(86) PCT No.: PCT/EP2018/082631
§ 371 (c)(1),
(2) Date: May 27, 2020

(87) PCT Pub. No.: WO2019/110363
PCT Pub. Date: Jun. 13, 2019

(65) Prior Publication Data
US 2020/0395108 A1  Dec. 17, 2020

(30) Foreign Application Priority Data
Dec. 6, 2017 (EP) .................................... 17205692

(51) Int. Cl.
| | |
|---|---|
| *G16H 10/00* | (2018.01) |
| *G16H 10/65* | (2018.01) |
| *G16H 40/67* | (2018.01) |
| *A61F 13/00* | (2006.01) |
| *A61F 13/15* | (2006.01) |

(52) U.S. Cl.
CPC ....... *G16H 10/65* (2018.01); *A61F 13/00051* (2013.01); *G16H 40/67* (2018.01); *A61F 2013/00817* (2013.01); *A61F 2013/15024* (2013.01)

(58) Field of Classification Search
CPC .. G16H 10/65; G16H 40/67; A61F 13/00051; A61F 2013/00817
See application file for complete search history.

(56) References Cited

U.S. PATENT DOCUMENTS

| | | | |
|---|---|---|---|
| 4,669,460 A | 6/1987 | Silber | |
| 10,158,928 B2 * | 12/2018 | Duesterhoft | ............. H04Q 9/00 |

(Continued)

FOREIGN PATENT DOCUMENTS

WO  WO-2016/138194 A1  9/2016

OTHER PUBLICATIONS

International Search Report and Written Opinion dated Dec. 21, 2018 by the International Searching Authority for International Application No. PCT/EP2018/082631, filed on Nov. 27, 2018 and published as WO 2019/110363 on Jun. 13, 2019 (Applicant—Mölnlycke Health Care AB) (13 Pages).

*Primary Examiner* — Tammara R Peyton
(74) *Attorney, Agent, or Firm* — Ballard Spahr LLP (57) ABSTRACT

A medical dressing, specifically adapted to comprise a machine-readable tag for allowing efficient and safe inspection during use of the medical dressing is described. A medical dressing arrangement and to a computer implemented inspection method applied in conjunction with the medical dressing is also described.

18 Claims, 5 Drawing Sheets

(56) References Cited

U.S. PATENT DOCUMENTS

| | | | |
|---|---|---|---|
| 11,395,918 B2* | 7/2022 | Bogie | H05K 1/115 |
| 2013/0232761 A1* | 9/2013 | Warren | A61B 5/0082 |
| | | | 29/428 |
| 2015/0269322 A1 | 9/2015 | Lyons et al. | |
| 2017/0281073 A1 | 10/2017 | Drennan et al. | |

* cited by examiner

MEDICAL DRESSING HAVING IDENTIFIABLE INFORMATION TAG THAT IS ONLY READABLE IF PORTION OF DRESSING IS EXPOSED

CROSS-REFERENCE TO RELATED APPLICATIONS

This application is a U.S. National Phase Application of International Application No. PCT/EP2018/082631, filed Nov. 27, 2018, which claims priority to European Application No. 17205692.1, filed Dec. 6, 2017, each of which are hereby incorporated by reference in their entirety.

TECHNICAL FIELD

The present disclosure generally relates to a medical dressing, specifically adapted to comprise a machine-readable tag for allowing efficient and safe inspection during use of the medical dressing. The present disclosure also relates to a computer implemented inspection method applied in conjunction with the medical dressing.

BACKGROUND

A pressure ulcer is a localized injury to the skin and/or the underlying tissue that results from pressure, typically in combination with friction and shear. Several factors can lead to pressure ulcers or pressure injuries, such as high pressure, uneven pressure distribution, disturbed microclimate, friction at the skin, and internal shear stresses. Pressure ulcers often arise among persons being bedridden for various reasons, such as for instance due to long term hospitalization or other causes of immobility. When the same location on the body is exposed to sustained pressure and shear, a pressure ulcer can develop in that location. Pressure ulcers typically develop in soft tissue under skin that covers bony areas of the body, for example the heels, ankles, the hips or the sacral buttocks. The necrosis in soft tissue spreads to the skin resulting in the formation of a pressure ulcer. Patients particularly at risk are those suffering from diabetes, cardiovascular conditions, incontinence, and arthritis.

The sacrum is an area that has a higher risk of developing pressure ulcers than other areas. The anatomy and physiology of the sacrum make the tissue very vulnerable to pressure. Patients that have been hospitalized or bedridden for a longer period require additional precautions to prevent sacrum ulceration. While pressure causes compression of the tissues, shear forces occur between the layers of the tissues and tend to tear and separate them. A pressure ulcer may originate in the soft tissue (fat or muscle) in the sacrum region, and spread to the skin, where it becomes visible. Not only does a pressure ulcer cause great discomfort and/or pain to the affected person, but it also causes difficulties to nursing personnel and/or other caregivers. In addition, pressure ulcers represent a big challenge to the healthcare system and are associated with high costs.

Pressure ulcers are largely preventable. When pressure ulcers occur, they can become painful wounds that require months to heal. In a hospital or care facility, caregivers adhere to specific protocols to prevent the occurrence of pressure ulcers. One important part in the prevention regimen is regular inspection of the skin. In some hospitals, the caregivers apply dressings to areas at risk of developing pressure sores. The dressings used are primarily designed to handle blood and body exudates stemming from existing wounds, scars or blisters and not for prophylactic purposes.

Furthermore, when a dressing has been applied, the skin underneath the dressing must be regularly inspected, typically at least twice a day, to assess the skin status and the potential progress of a pressure ulcer. The inspection of the skin area requires the dressing to be opened, and detached from the skin. One option would be to remove the dressing and apply a new dressing after having checked the relevant skin area. However, this is both costly and time consuming. Alternatively, nursing personnel may detach the dressing by gripping and lifting an adhesive border of the dressing (i.e. the portion of the dressing surrounding the pad) so that the relevant skin area can be checked, and then the dressing can be re-applied by re-attaching the adhesive border to the surrounding skin.

With the above in mind, it may be desirable to provide means for allowing the regular inspections to be performed caregivers and staff in the most efficient and safe manner.

SUMMARY

In view of above-mentioned and other drawbacks of the prior art, it is an object of the present disclosure to provide improvements in relation to efficient and safe inspection during use of the medical dressing, for example preventatively applied to an area where a pressure ulcer possibly may develop.

According to an aspect of the present disclosure, it is therefore provided a medical dressing having a first side and a second opposing side, the first side comprises an adhesive layer having a skin-facing surface adapted to detachably adhere the medical dressing to a dermal surface, the medical dressing further comprising a first tag, wherein the first tag holds identifiable information that is readable, using an electronic device, only if a predetermined portion of the skin-facing surface is detached from the dermal surface.

The present disclosure is based upon the realization that a machine-readable tag, i.e. the above defined first tag that is readable using the electronic device, may be "strategically" positioned such that the first tag only is readable if a predetermined portion of the medical dressing is detached from an area (skin) of a patient where the medical dressing has been applied. Accordingly, by such an implementation it may as a consequence be possible to control and log when (and possibly by whom) the medical dressing was "removed" from patient during one of the regular inspections as was discussed above. The above defined adhesive layer typically allows the medical dressing to be repeatedly (at least partly) removed and re-applied to the dermal surface (of the patient).

The identifiable information may for example comprise individualized information related to the first tag, whereby different first tags arranged at different medical dressings may be separated. An advantage following the individualization for a specific first tag is that it may be possible to ensure that nursing personnel and/or other caregivers in fact have performed an inspection, for example in line with a predefined scheme and/or prevention compliance protocols in place, for when and at what interval the inspection should take place (such as by means of a reminder/notification). The individualized information comprised with the first tag may further be allowed to form a "relation" between a specific first tag, the nursing personnel and/or other caregivers performing/in charge of the inspection, as well as to when the inspection was performed. In addition, using an electronic device for reading/scanning the first tag once the predetermined portion of the medical dressing has been detached (from the dermal surface) may open for further possibilities, such as e.g. acquiring media content (such as an image, a video sequence, etc.) of an "exposed skin area".

In a possible embodiment of the present disclosure, the identifiable information of the first tag is readable only if the predetermined portion of the skin-facing surface is visibly observable, such as if at least 25% (or 40%, or even more) of the adhesive layer is detached from the dermal surface. In one embodiment of the present disclosure, the first tag may possibly be positioned "centrally" of the medical dressing such that at least 50% (if seen sideways) needs to be detached from the dermal surface (skin of the patient) before the first tag is readable using the electronic device.

The concept according to the present disclosure is not specifically limited towards use of a specific type of technology for the first tag or for how to "read/scan" the first tag. Rather, the machine readable first tag may be implemented based on different technology.

In one embodiment, the first tag is optically readable using the electronic device, for example implemented as at least one of a one-dimensional (1D) and a two-dimensional (2D) bar code. Other optical methods, present and future, may be possible and are within the scope of the present disclosure. In case of using an optically readable tag, possibly a so called QR code, it is desirable to equip the electronic device with e.g. a camera or similar means for capturing the optically readable first tag. The electronic device may also be provided with means (such as a light source) for ensuring that "enough" light is provided when capturing the optically readable first tag.

As an alternative, or also, the first tag may be adapted to employ radio frequency (RF) communication, such as by arranging the first tag to be at least one of a radio-frequency identification (RFID) tag and a near field communication (NFC) tag. In such an embodiment, it may be suitable to arrange such that e.g. an antenna comprised with the RFID or the NFC tag is "shielded" such that the tag may only be readable when "enough" of the medical dressing has been released from the dermal surface.

In a possible embodiment of the present disclosure it may be possible to also include a second tag with the medical dressing. The second tag is typically readable "at all time", i.e. not only when the predetermined portion of the skin-facing surface is detached from the dermal surface. The second tag may for example be used for identifying a type of the medical dressing, not necessarily holding any specific individualized information relating to the specific medical dressing, but rather e.g. providing generic information relating to the type of the medical dressing. The second tag may in a corresponding manner as the first tag possibly be at least one of a one-dimensional (1D) and a two-dimensional (2D) bar code or is adapted to employ radio frequency (RF) communication. The second tag may in some embodiments be arranged to the second side of the medical dressing, i.e. the side of the medical dressing that is not intended to face the dermal surface/skin of the patient. The second tag may alternatively be comprised with e.g. a packaging for the medical dressing, whereby identifiable information that is comprised with the second tag possibly may be read (only) at the time of removing the packaging from the medical dressing before attaching the medical dressing to the patient.

Furthermore, in a possible embodiment of the present disclosure the first tag is comprised as a component of the medical dressing. That is, the first tag may be "integrated with" the medical dressing during manufacturing of the medical dressing, as will be elaborated below.

In another possible alternative embodiment of the present disclosure it may be possible to allow the first tag to be attachable to the medical dressing. That is, the first tag must not necessarily be integrated with the medical dressing but may rather be provided as an "add on", for example arranged as a "sticker" that is to be attached to the first side of the medical dressing. That is, in such an embodiment, it may for example be possible to provide the skin-facing surface (first side) with a marking or similar for allow e.g. the nursing personnel and/or other caregivers to correctly attach the first tag to the medical dressing before the first time the medical dressing is attached to the area of the patient in a manner as discussed above. Such an embodiment may be specifically advantageous in situations where the patient e.g. is determined to be a "high risk" patient that requires extra precautions and inspections (i.e. patients at high risk of developing pressure ulcers).

In addition to the above, it may in one possible embodiment of the present disclosure be advantageous to allow the medical dressing to further comprise at least one gripping tab, wherein the gripping tab may be arranged coplanar with and projecting outwardly from a periphery of the medical dressing. The purpose with the at least one gripping tab is to simplify the process for the nursing personnel and/or other caregivers when performing the regular inspections, by making the detaching and adequate re-applying of the medical dressing easier. Furthermore, nursing personnel and/or other caregivers may also have a guide with respect to where to start detaching the medical dressing. Adequate detaching and reapplying of the medical dressing results in longer stay-on ability of the medical dressing and less frequent need for replacing an old dressing with a new one. The gripping tab guides the nursing personnel and/or other caregivers to lift the dressing, inspect the skin underneath the dressing, and to thereafter re-apply the dressing onto the skin (in case the skin "looks ok").

Since the inspection of the skin typically takes place where the patient is lying on the side in the bed, it is beneficial to have at least two gripping tabs such that the caregiver can lift the dressing regardless of which side the patient lies. The second gripping tab may thus be arranged opposite the first gripping tab at the medical dressing. The medical dressing may likewise be provided with more than a single first tag, such as two first tags.

The medical dressing may form part of a dressing arrangement further comprising the electronic device as discussed above, where the electronic device comprises means for reading the identifiable information of the first tag. The means for reading the identifiable information of the first tag is typically dependent on the technology used for the first tag, e.g. adapted to optically read the first tag or for communicating with the first tag using RF communication. As such, the electronic device may for example be equipped with a camera or similar for optically reading the first tag and/or a RF transceiver adapted for wireless communication with the first tag.

In a possible embodiment of the present disclosure the electronic device is a mobile electronic device, such as e.g. at least one of a "dedicated electronic device", a mobile phone, a tablet, etc. The electronic device may as an alternative be computer (e.g. laptop) provided with one of the above-mentioned means for reading the identifiable information of the first tag.

In a preferred embodiment of the present disclosure the electronic device comprises a graphical user interface (GUI) adapted to provide a user with an instruction to read the identifiable information of the first tag. The GUI may for example be adapted to instruct the nursing personnel and/or other caregivers when to perform the (regular) inspection of the dermal surface (of the patient). The GUI may also be adapted to provide the nursing personnel and/or other caregivers with instructions to e.g. capture an image of the dermal surface of the patient at the time of inspection.

The GUI may also be adapted to allow e.g. the nursing personnel and/or other caregivers the option to input e.g. patient specific information related to the patient's risk of developing pressure ulcers (weight, condition, diseases, Braden score). Such information may thus then be allowed to be "viewed" by e.g. a different nursing personnel at a later point in time for assisting that different nursing personnel in further handling of the patient.

The medical dressing arrangement may in turn form part of a medical dressing system, further comprising a server arranged in communication with the electronic device, wherein the server is adapted for storage of the identifiable information of with the tag and a time/date of reading the identifiable information. Accordingly, once the nursing personnel and/or other caregivers operating the electronic device has inspected "beneath" the coverage area of the medical dressing, data relating to the same may be (e.g. automatically) uploaded to the server/digital storage, possibly allowing for logging and further processing to take place. The information presented at the GUI of the electronic device may also be provided, possibly on an individualized level, to the nursing personnel and/or other caregivers from the server/digital storage.

According to another aspect of the present disclosure, there is further provided a method for reading a first tag holding identifiable information, wherein the first tag is comprised with a medical dressing, the medical dressing having a first side and a second opposing side, the first side comprises an adhesive layer having a skin-facing surface adapted to detachably adhere the medical dressing to a dermal surface, wherein the method comprises the steps of receiving, at an electronic device, a request to read the identifiable information of the first tag, and reading, using the electronic device, the identifiable information of the first tag, wherein the identifiable information is readable only if a predetermined portion of the skin-facing surface is detached from the dermal surface. This aspect of the present disclosure provides similar advantages as discussed above in relation to the previous aspects of the present disclosure. The method may for example be computer implemented.

In an embodiment, it may be possible to further allow the method to comprise the step of detaching the predetermined portion of the skin-facing from the dermal surface.

According to a still further aspect of the present disclosure, there is provided a method for reading a first tag holding identifiable information, wherein the first tag is comprised with a medical dressing, the medical dressing having a first side and a second opposing side, the first side comprises an adhesive layer having a skin-facing surface adapted to detachably adhere the medical dressing to a dermal surface, wherein the method comprises the steps of receiving, at an electronic device, a request to read the identifiable information of the first tag, detaching a predetermined portion of the skin-facing from the dermal surface, and reading, using the electronic device, the identifiable information of the first tag, wherein the identifiable information is readable only if the predetermined portion of the skin-facing surface is detached from the dermal surface. Also this aspect of the present disclosure provides similar advantages as discussed above in relation to the previous aspects of the present disclosure.

Further features of, and advantages with, the present disclosure will become apparent when studying the appended claims and the following description. The skilled addressee realizes that different features of the present disclosure may be combined to create embodiments other than those described in the following, without departing from the scope of the present disclosure.

BRIEF DESCRIPTION OF THE DRAWINGS

The various aspects of the present disclosure, including its particular features and advantages, will be readily understood from the following detailed description and the accompanying drawings, in which.

DETAILED DESCRIPTION

The present disclosure will now be described more fully hereinafter with reference to the accompanying drawings, in which currently preferred embodiments of the present disclosure are shown. The present disclosure may, however, be embodied in many different forms and should not be construed as limited to the embodiments set forth herein; rather, these embodiments are provided for thoroughness and completeness, and fully convey the scope of the present disclosure to the skilled person. Like reference characters refer to like elements throughout.

Figure 1A:
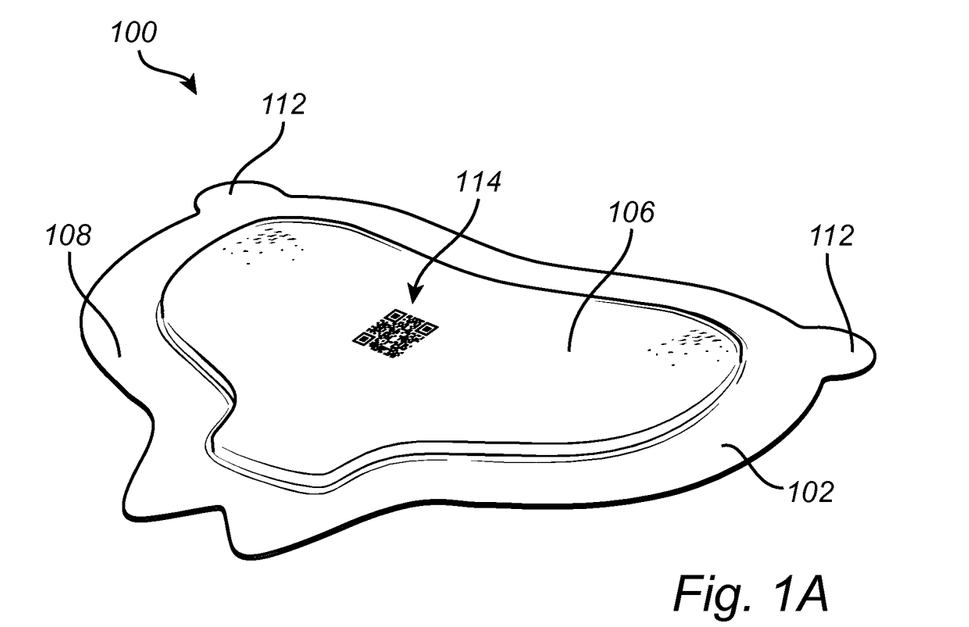
FIGS. 1A and 1B presents exemplary illustrations of a top and a bottom side, respectively, of a medical dressing according to an embodiment of the present disclosure.
Figure 1B:
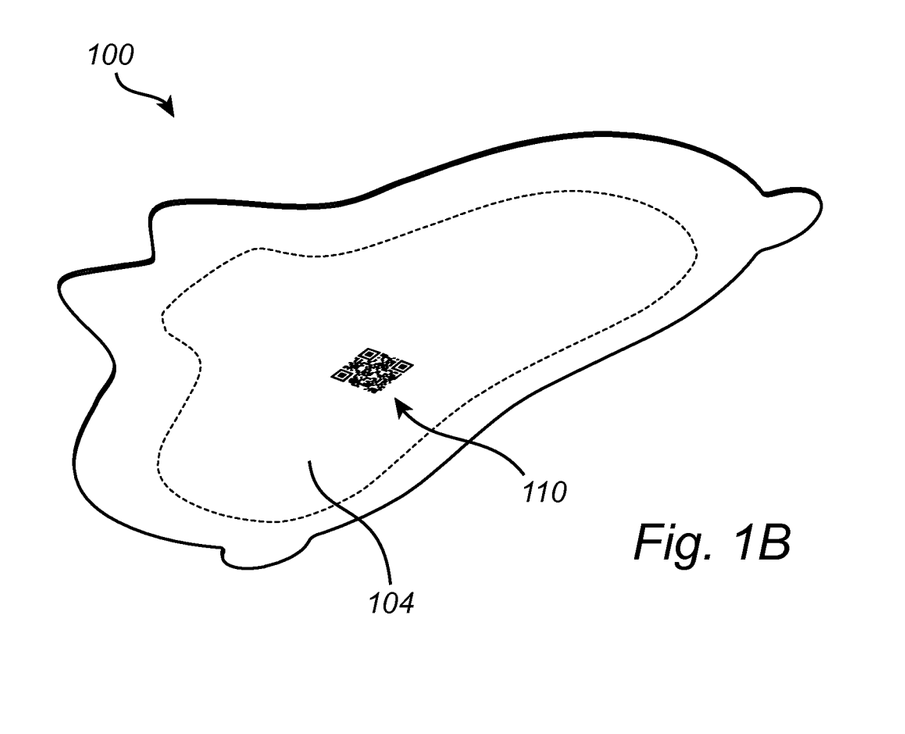

Turning now to the drawings and to FIGS. 1A and 1B in particular, there is conceptually illustrated an exemplary illustration of a medical dressing 100 according to the present disclosure for application to a contoured surface, such as the sacrum of a wearer/patient.

The medical dressing 110 is defined to have a first side and a second opposing side. The first side is below referred to as a "bottom side", intended to face towards a dermal surface/skin of the wearer/patient during use of the medical dressing. Accordingly, the opposing second side of the medical dressing 100 is thus intended face away from the dermal surface/skin of the wearer/patient during use of the medical dressing 100. For ease of understanding, in the illustrations FIG. 1A is showing the top side of the medical dressing 100 facing towards a viewer of the Figs. Correspondingly, FIG. 1B is showing the bottom side of the medical dressing 100 facing towards the viewer.

The medical dressing 100 comprises a backing layer 102, an adhesive body contact layer 104 and a pad 106, in the exemplary embodiment as shown in FIG. 1A arranged in the central portion between the backing layer 102 and the body contact layer 104. The backing layer 102 and the body contact layer 104 extend beyond the periphery of the pad 106 to define a border portion 108 along the contour of the pad 106. As used herein, the term "body contact layer" means the layer that is in contact with the dermal surface/skin of the wearer/patient.

The medical dressing 100 according to the present disclosure further comprises a first tag 110 arranged at the bottom side of the medical dressing 100. The first tag 110 may in one embodiment comprise an optically machine readable tag such as a one-dimensional (1D) and a two-dimensional (2D) bar code. In the illustration shown in FIG. 1B the first tag 110 is a 2D bar code, specifically illustrated as a so called QR code.

In line with the present disclosure the optically readable first tag 110 may for example be printed or dyed at the body contact layer 104. That is, it may for example be possible to apply a "screen printing process" (or similar) for forming the printed or dyed first tag 110, which in some embodiments may be preferred. At the same time, it should be understood that the first tag 110 may be somewhat integrated with the substrate, for example formed at the manufacturing of the substrate.

It should further be understood that the first tag 110 could be printed or dyed at either side of the body contact layer 104. For example, the body contact layer 104 may be somewhat transparent, whereby the first tag 110 may be printed or dyed on a side of the body contact layer 104 facing away from the dermal surface/skin of the wearer/patient during use of the medical dressing 100, whereby the first tag 110 is adapted to be optically readable "through" the body contact layer 104. The first tag 110 may of course in an alternative embodiment be printed or dyed on the other side, i.e. on the side facing towards the dermal surface/skin of the wearer/patient during use of the medical dressing 100. In an embodiment of the present disclosure the first tag 110 is integrated with the medical dressing 100 by means of printed the first tag 110 at or in the vicinity of the body contact layer 104. The first tag 110 may alternatively be arranged "underneath" at least a portion of the body contact layer 104 in case the (portion of the) body contact layer 104 for example is at least partly perforated or at least partly optically transparent.

The first tag 110 is adapted to hold an amount of identifiable information that may be read by an electronic device when the electronic device is arranged on a vicinity of the first tag 110. Specifically, in accordance to the present disclosure the first tag 110 is illustrated as arranged centrally at the bottom side of the medical dressing 100. Accordingly, during use of the medical dressing 100, the first tag 108 will be essentially "hidden" from e.g. nursing personnel and/or other caregivers.

It should be understood that the first tag 110 not necessarily must be arranged exactly centrally at the medical dressing 100; rather the first tag 110 may also be arranged slightly of center. It should further be understood that the medical dressing 100 may be provided with (comprise) more than a single first tag 110. For example, the medical dressing 100 may be provided with two of such first tags 110 (not explicitly shown) arranged slightly of center, thus possibly only making one of the two first tags 110 accessible when the wearer/patient is lying on the side. An inspection may in such an embodiment possibly comprise scanning both of the first tags 110.

As defined above and as illustrated in FIG. 1B, the first tag 110 is arranged/positioned such that the identifiable information stored with the first tag 110 may not be read during normal use of the medical dressing 100, i.e. once the bottom side of the medical dressing 110 is in contact with the skin of the wearer/patient. Accordingly, it will be necessary for the nursing personnel and/or other caregivers to carefully remove at least a portion of the medical dressing 100 to make it possible for the identifiable information comprised with the first tag 110 to be read. Such a procedure is normally performed when inspecting the skin of the wearer/patient. Thus, at the time of removing a portion of the medical dressing 100 from the skin of the wearer/patient also the first tag 110 is made accessible and thus the identifiable information of the first tag 110 may be read.

For assisting the nursing personnel and/or other caregivers to carefully remove the medical dressing 100 from the skin of the wearer/patient, the medical dressing 100 may be provided with at least one gripping tab 112, e.g. forming an extension of the border portion 108, as will be further discussed below.

In case of the medical dressing 100 comprising an optically readable first tag 110, the first tag 110 will accordingly have to be at least partly optically visible for the nursing personnel and/or other caregivers, and thus the nursing personnel and/or other caregivers may position the electronic device in such a manner that the identifiable information stored with the first tag 110 may be read. It should however be understood that the first tag 110 is not limited to be implemented as an optically machine readable tag, rather other technologies may be used for the same purpose. One example of such an alternative technology is to make use of a first tag that is arranged to employ radio frequency (RF) communication (wireless) with the electronic device. Different RF based technologies exist, including for example radio-frequency identification (RFID) tags or near field communication (NFC) tags. Other possibilities may be possible, including for example Bluetooth, etc.

In case of employing RF technology, it may be desirable to "shield" any wireless signals coming from/to the RF based first tag, such that the wireless signals only are transmitted/received when at least a predetermined portion of the medical dressing 100 has been removed from the skin of the wearer/patient. The shield may in one embodiment comprise e.g. a metal sheet, such as a thin aluminum foil. It may also be possible to arrange an antenna comprised with the RF based first tag to be somewhat directional, meaning that wireless communication with the RF based first tag is only possible once the predetermined portion of the medical dressing 100 has been removed from the skin of the wearer/patient.

As explicitly discussed above, the first tag 110 may be arranged as a component of the medical dressing 100, i.e. integrated with the medical dressing 100 and possibly integrated with the medical dressing 100 during manufacturing of the medical dressing 100. However, the first tag 110 may as an alternative be later affixed to the side of the medical dressing 100 facing the skin of the wearer/patient. As such, the first tag 110 may be provided as a separate component to be affixed to the medical dressing 100, typically before initial use of the medical dressing 100.

As has been indicated above, the medical dressing 100 may also comprise a second tag 114. Contrary to the first tag 110, the second tag 114 is not intended to be "hidden" during normal use of the medical dressing 100. Rather, the second tag 114 may for example be positioned as exemplified in FIG. 1A, where the second tag 114 is provided at the top side of the medical dressing 100, whereby the second tag 114 is typically readable "at all time", i.e. not only when the predetermined portion of the skin-facing surface is detached from the dermal surface. The second tag 114 must not necessary hold any individualized information relating to the specific medical dressing (such as may be possible in regards to the first tag 110), but rather providing generic information relating e.g. to the type of the medical dressing 100.

The second tag 114 may in a corresponding manner as the first tag possibly be at least one of a one-dimensional (1D) and a two-dimensional (2D) bar code or is adapted to employ radio frequency (RF) communication. It should be understood that the second tag 114 not necessarily must be comprised with the medical dressing 100. Rather, the second tag 114 may possibly, as an alternative (or also), be comprised with e.g. a packaging (not shown) for the medical dressing 100, whereby identifiable information that is comprised with the second tag 114 possibly may be read (only) at the time of removing the packaging from the medical dressing 100 before attaching the medical dressing to the wearer/patient.

Figure 2A:
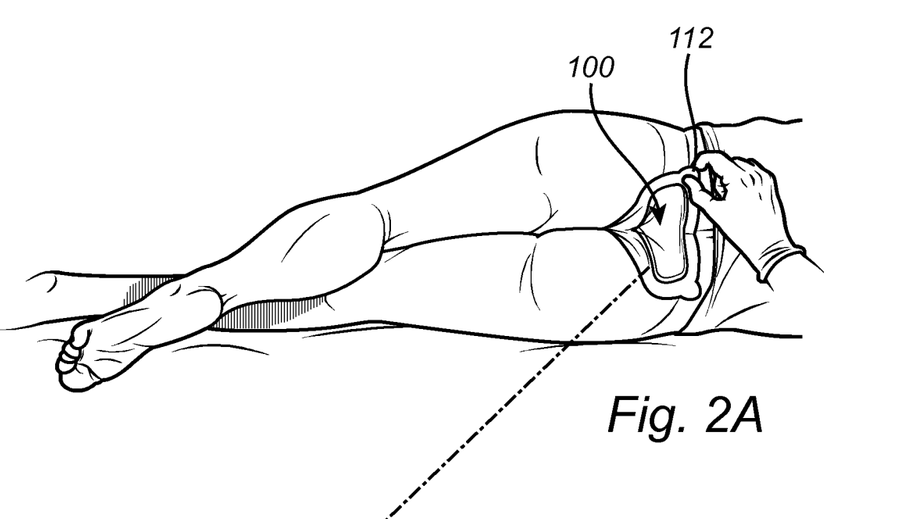
FIG. 2A shows a medical dressing according to an exemplary embodiment of the invention, the dressing having been applied to the sacrum region of a human body.
Figure 2B:
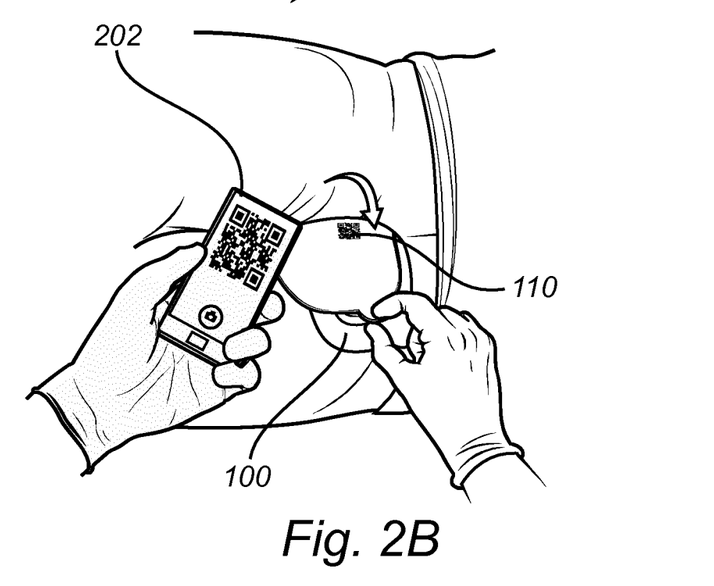
FIG. 2B is a detailed view of the dressing in FIG. 2A, illustrating inspection of the skin of the wearer.

FIGS. 2A and 2B illustrates a wearer/patient lying on the side (as briefly mentioned above), which is often the case for patients at risk of e.g. developing pressure ulcers. The nursing personnel and/or other caregivers may for example use a hand to lift the gripping tab 112 of the medical dressing 100 and partially remove the medical dressing 100 from the skin of the wearer/patient for allowing the skin that was previously underneath the medical dressing 100 to be inspected. As explained above, due to the positioning/arrangement of the first tag 110, it will only be possible to read the identifiable information comprised with the first tag 110 once the first tag 110 is at least partly exposed (FIG. 2B). Once the skin has been checked, the medical dressing 100 may be re-applied to the skin or taken off if needed.

As also mentioned above, since the identifiable information comprised with the first tag 110 only is accessible to be read by an electronic device 202 once at least a portion of the first tag 110 has been exposed, it may be possible to ensure that nursing personnel and/or other caregivers in fact performed an inspection in fact was performed, for example in line with a predefined scheme, prevention compliance protocols in place, for when and at what interval the inspection should take place. Thus, the individualized information comprised with the first tag 110 may be used to form a relation between a specific first tag 110, the nursing personnel and/or other caregivers, and when the inspection was performed in regards to the medical dressing comprising the specific first tag 110. Even though not explicitly shown in FIGS. 2A and 2B, in some embodiment of the present disclosure an inspection comprises scanning both of the first 110 and the second 114 tag.

Figure 3A:
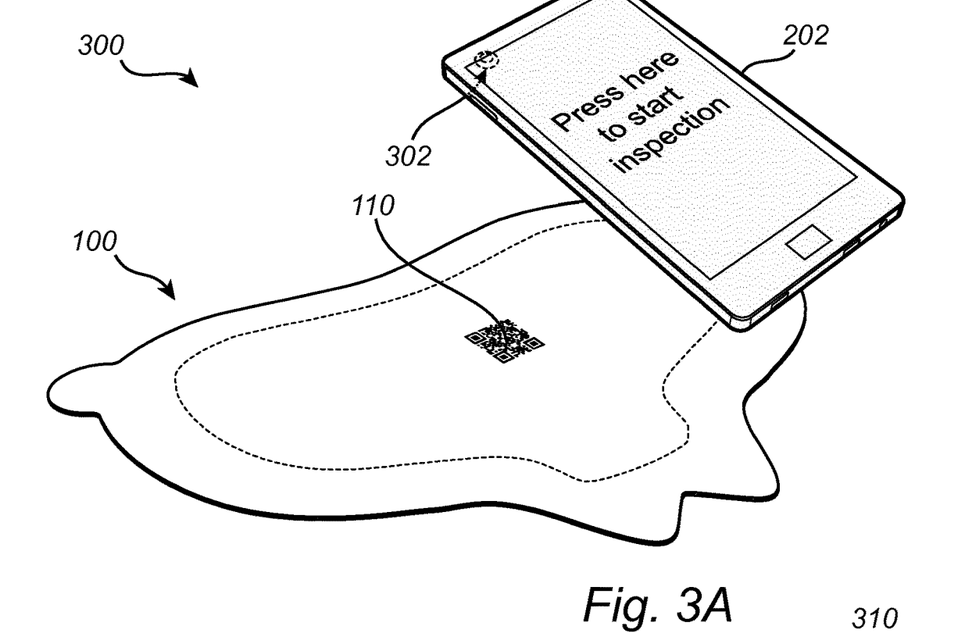
FIGS. 3A and 3B show a medical dressing arrangement and a medical dressing system, respectively, provided in line with the concept of the present disclosure.

Turning now to FIG. 3A, conceptually illustrating a medical dressing arrangement 300 according to a currently preferred embodiment of the present disclosure. The medical dressing arrangement 300 comprises a medical dressing 100 as well as the electronic device 202. In FIG. 3A the electronic device 202 is shown as a generic electronic device in the form of a mobile phone. It should however be understood that any type of generic or specifically adapted electronic device may be used in line with the concept of the present disclosure.

Using such a generic electronic device may in some instances be preferred for the ease of use and the simplicity of developing software suitable for reading and processing the identifiable information stored with the first tag 110. It may however in some instances be more suitable to use a specifically adapted electronic device in the form of a dedicated medical electronic device, possibly due to security or privacy reasons.

In FIG. 3A, the electronic device 202 is provided with a camera 302 and a light source (not explicitly shown). During operation of the electronic device 202, the nursing personnel and/or other caregivers operating the electronic device 202 may activate a software application (e.g. "App") installed at the electronic device 202. The App may in turn activate the camera 302 and possibly the light source. The camera 302 is then to be pointed towards the exposed first tag 110 comprised with the medical dressing 100. The camera 302 will then capture an image of the first tag 110, and the electronic device 202 will, in accordance to known image processing schemes, extract the identifiable information comprised with the first tag 110 from the captured image.

In a possible embodiment, the electronic device 202 (and thus the App) may be adapted to determine if an "enough" amount of the medical dressing 100 has been removed from the dermal surface/skin of the wearer/patient. Accordingly, it may be allowed to restrict the capturing of the mentioned image of the first tag 110 to only when an adequate amount of the skin of the wearer/patient has been exposed. Such a determination may be performed using an image processing scheme implemented as a component of the App.

In case of using an RF based first tag, it is desirable to provide the electronic device with means (such as a wireless transceiver) adapted for wireless communication with e.g. the RFID or NFC tag.

Figure 3B:
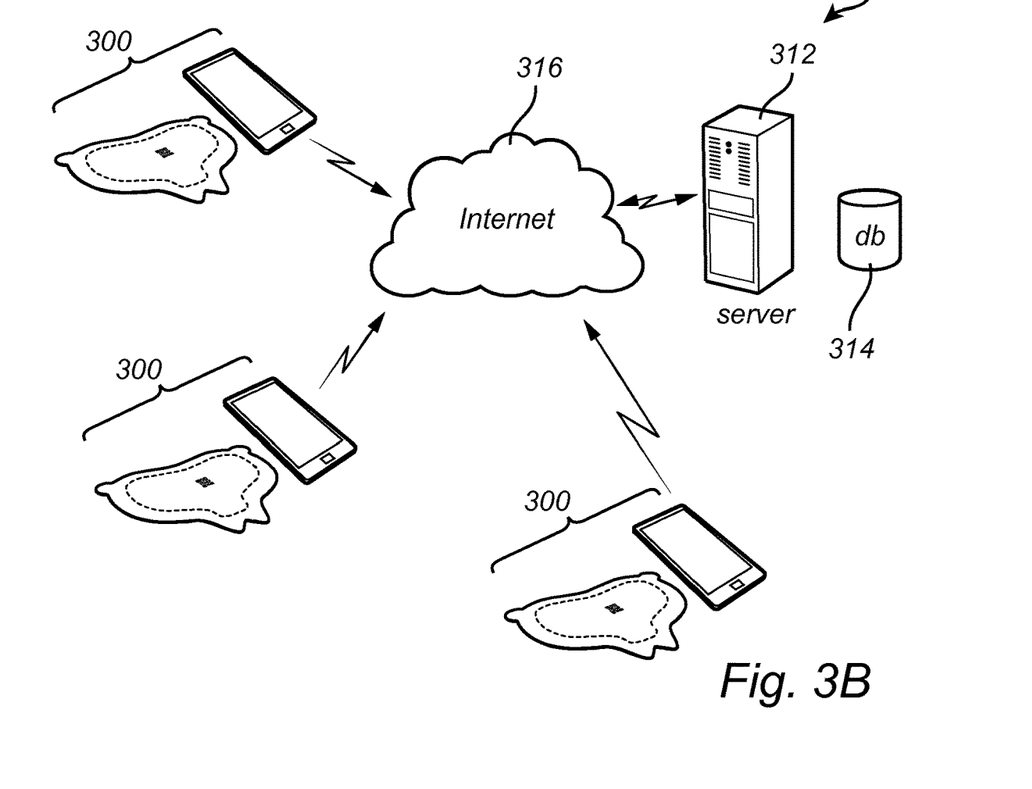

In FIG. 3B the medical dressing arrangement 300 is shown as a component of a medical dressing system 310. The medical dressing system 310 further comprises a server 312 and a thereto connected database 314. The electronic device 202 (such as the mentioned mobile phone) comprised with the medical dressing arrangement 300 is generally provided with communication means allowing the electronic device to, e.g. wired or wirelessly, communicate with the server 312, for example using a network connection such as the Internet 316.

Accordingly, once the identifiable information has been collected by the electronic device 202 from the first tag 110 comprised with the medical dressing 100, this information is transmitted over the Internet 316 to the server 312 for storage at the database 314. It may of course be possible to allow the network connection to be limited to within a specific site, such as a hospital, thus not allowing any information to leave the specific site. In such a case, it may be desirable to allow the server 312 and the database 314 to be arranged at the specific site.

Once the information is stored at the server 314, it may be possible to process the information to form e.g. a log of when the identifiable information form the first tag 100 was read (time, date), by whom, for what wearer/patient, etc. The log may for example be accessible by staff members to ensure that the reading of the first tag 100 and thus the inspection of the skin underneath the medical dressing 100 has been performed, such as in line with a scheme applied/developed by the above-mentioned hospital and/or the manufacturer of the medical dressing 100.

It should be understood that the medical dressing system 310 may comprise more than a single medical dressing arrangement 300. For example, the medical dressing system 310 may be adapted to comprise a plurality of medical dressing arrangements 300 arranged in networked communication with the server 312 and the database 314. Accordingly, information collected from different wearers/patients provided with the medical dressing 100, 200, may be processed at the server 312/database 314. Such an implementation may possibly allow for correlations to be made based on the collected information. The identifiable information from the first tag 110 may of course also or alternatively be stored locally with the electronic device 202.

Turning now to FIGS. 4A-4E, presenting exemplary views of a graphical user interface (GUI) 402 that may be comprised with the above mentioned App that has been installed with the electronic device 202.

Figure 4A:
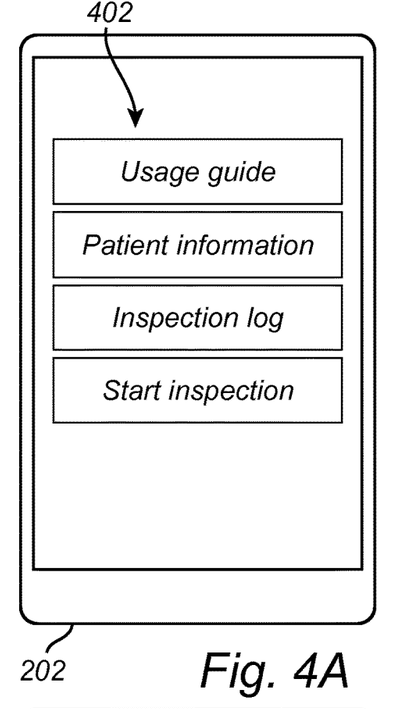
FIGS. 4A-4E exemplifies different views of a GUI presented at an electronic device comprised with the medical dressing arrangement of FIG. 3A.

FIG. 4A shows a possible "start interface" for operating a plurality of different services that may be provided by means of the App and the thereto related GUI 402. Specifically, the start interface lists four different exemplary services that may be activated by pressing a dedicated button at the GUI 402. The exemplary start interface comprises, but is not limited to, a usage guide (see further FIG. 4B), means for acquiring and/or providing patient information (see further FIG. 4C), an inspection log (see further FIG. 4D), and an activation of the inspection (see further FIG. 4E).

Figure 4B:
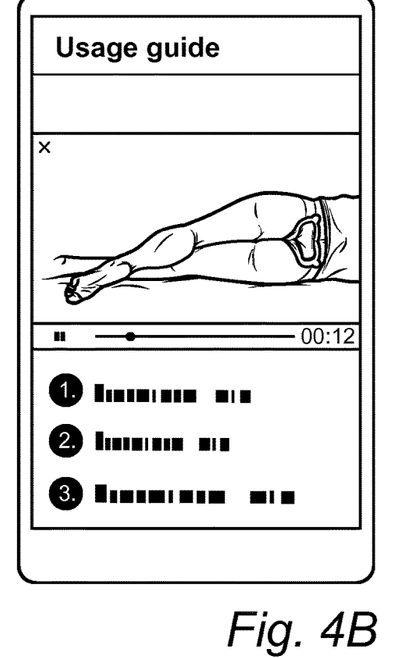

In FIG. 4B there is provided an exemplary view of the GUI 402 presenting the usage guide for the nursing personnel and/or other caregivers. The usage guide may for example be adapted to present information on how to affix the medical dressing 100 to the wearer/patient, how to perform the above discussed inspection of the skin of the wearer/patient, etc. Such an instruction may for example comprise a still image and/or video based instruction (and/or still images combined with text) on how to perform the inspection.

Figure 4C:
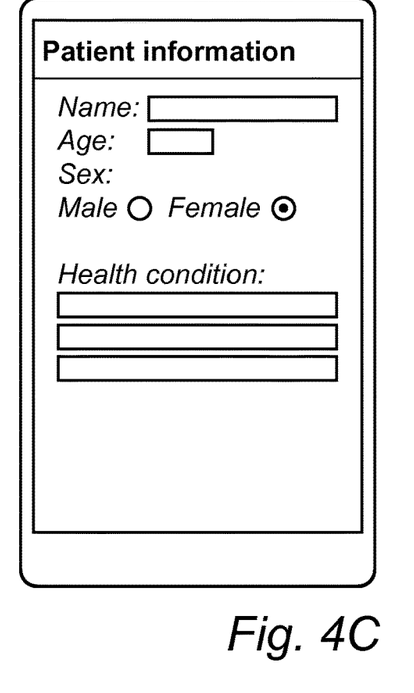

In FIG. 4C there is provided an exemplary view of the GUI 402 presenting means for acquiring and/or providing patient information. For example, this view may hold information relating to the name, age or sex of the wearer/patient. However, it may also be possible to allow this view to present information relating to e.g. a health condition of the wearer/patient, potential diseases, patient Braden score (which may be used as a measure of the patient's risk of developing pressure ulcers). This view may also be adapted to allow the nursing personnel and/or other caregivers to input e.g. contextual information relating to the wearer/patient, such as in relation to useful notes on skin color, skin appearance and texture, potential wound development or size of existing wound. This facilitates the complete inspection scheme and facilitates for the next nursing personnel and/or other caregivers assigned to perform a future (the next) inspection.

Figure 4D:
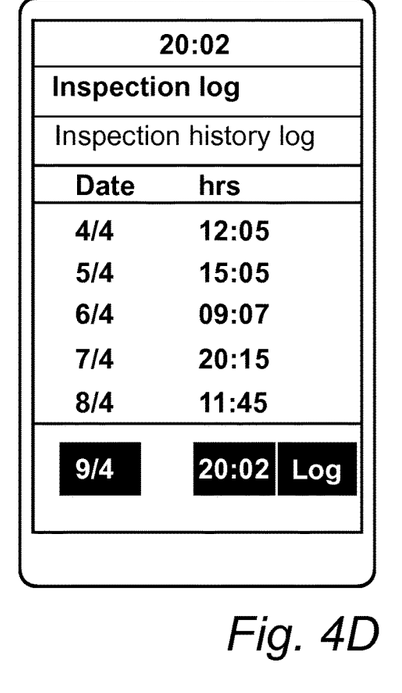

In FIG. 4D there is provided an exemplary view of the GUI 402 presenting an inspection log, typically comprising information relating to previously performed inspections. For example, the previous inspections may possibly be listed with at least some form of information relating to when the inspection was performed, such as a date and time when the previous inspection was performed. It could also be possible to move further hierarchically into previous inspections, possibly allowing further detailed information relating to a specific inspection to be presented to the nursing personnel and/or other caregivers.

Figure 4E:
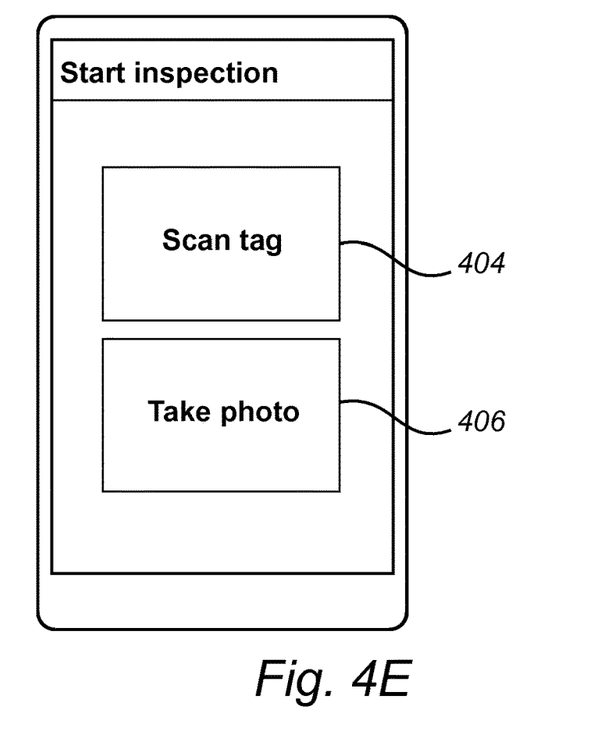

In FIG. 4E there is provided an exemplary view of the GUI 402 presenting an interface for performing an inspection as discussed above. For example, this view may comprise two buttons, where a first 404 of the two buttons is adapted to activate e.g. the camera 302 for optically reading the QR code based first tag 110 as provided at the bottom side of the medical dressing 100. The first button 404 could also possibly be used for activating e.g. means for reading a NFC based first tag 110.

A second 406 one of the two buttons may for example be provided for allowing the nursing personnel and/or other caregivers to take a video or a photo of the skin of the wearer/patient (e.g. using the camera 302), typically of an area that previously has been at least partly covered by the medical dressing 100 when affixed to the skin of the wearer/patient.

Figure 5:
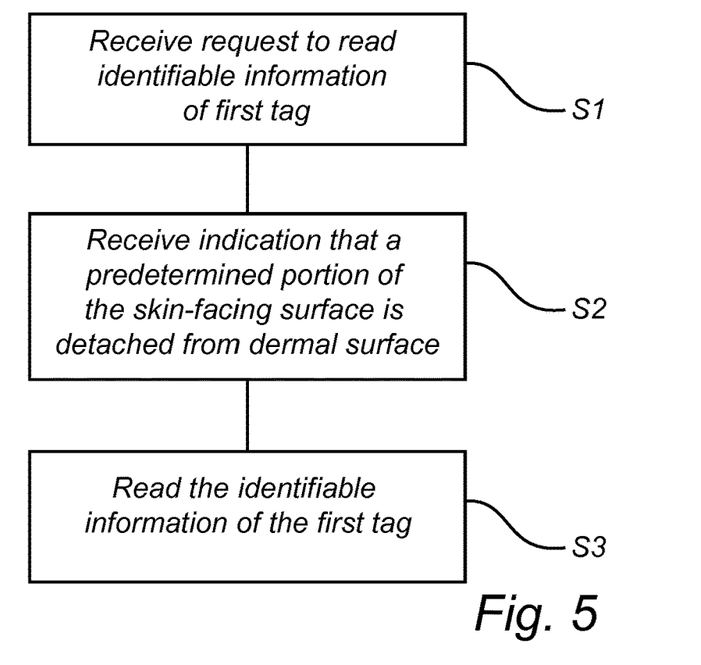
FIG. 5 is a flow chart illustrating the steps of performing the method according to a currently preferred embodiment of the present disclosure.

Turning now to FIG. 5, which presents a flow chart illustrating the steps of performing the method according to a currently preferred embodiment of the present disclosure. The method optionally starts with the GUI 402 presented at the display unit of the electronic device 202 presents the nursing personnel and/or other caregivers operating the electronic device 202 with a notice to perform an inspection in line with the above discussion. Once the nursing personnel and/or other caregivers has at least partly removed the medical dressing 100 from at least a predetermined portion of the skin of the wearer/patient, the electronic device 202 receives, S1, a request to read the identifiable information of the first tag 110. The request may for example be initiated by the nursing personnel and/or other caregivers pressing a button 404 shown within the GUI 402.

As mentioned above, the App executed at the electronic device 202 may be adapted to receive, S2, an indication that the predetermined portion of the medical dressing has been removed from the skin of the wearer/patient. This process may be automatic using e.g. the mentioned image processing scheme or manual or semi-manual initiated by the nursing personnel and/or other caregivers. Subsequently, the camera 302 (and optionally the light source) may be activated for reading, S3, the identifiable information of the first tag 110.

In line with the above discussion, the identifiable information may then be stored locally at the electronic device 202 and/or remotely at the server 312/database 314, typically together with a time/date of when the reading was performed. It may also be possible to capture and store further information, such as an image of the skin of the wearer/patient, video, text, audio, etc. to assist in caring for the wearer/patient.

In summary, the present disclosure relates to a medical dressing having a first side and a second opposing side, the first side comprises an adhesive layer having a skin-facing surface adapted to detachably adhere the medical dressing to a dermal surface, the medical dressing further comprising a first tag, wherein the first tag holds identifiable information that is readable, using an electronic device, only if a predetermined portion of the skin-facing surface is detached from the dermal surface.

The present disclosure is based upon the realization that a machine-readable tag, i.e. the above defined first tag that is readable using the electronic device, may be "strategically" positioned such that the first tag only is readable if a predetermined portion of the medical dressing is detached from an area of a patient where the medical dressing has been applied. Accordingly, by such an implementation it may consequently be possible to control and log when (and possibly by whom) the medical dressing was removed from patient during one of the regular inspections as was discussed above. The above defined adhesive layer typically allows the medical dressing to be repeatedly (at least partly) removed and re-applied to the dermal surface (of the patient).

The control functionality of the present disclosure may be implemented using existing computer processors, or by a special purpose computer processor for an appropriate system, incorporated for this or another purpose, or by a hardwire system. Embodiments within the scope of the present disclosure include program products comprising machine-readable medium for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor.

Although the figures may show a sequence the order of the steps may differ from what is depicted. Also, two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule-based logic and other logic to accomplish the various connection steps, processing steps, comparison steps and decision steps. Additionally, even though the present disclosure has been described with reference to specific exemplifying embodiments thereof, many different alterations, modifications and the like will become apparent for those skilled in the art.

For example, it should be understood that even though the medical dressing as described above and shown in the Figs. are intended to arrangement at the sacrum of a patient, it may also be possible to make use of the concept according to the present disclosure for medical dressings suitable for any part of the skin of the patient, such as e.g. the heels, knees, hips, chest, etc. Additionally, it should be understood that the concept according to the present disclosure is not restricted for mere purpose of preventing pressure ulcers, but may also be used in the treatment regimen of such ulcers or sores.

In addition, variations to the disclosed embodiments can be understood and effected by the skilled addressee in practicing the present disclosure, from a study of the drawings, the disclosure, and the appended claims. Furthermore, in the claims, the word "comprising" does not exclude other elements or steps, and the indefinite article "a" or "an" does not exclude a plurality.

The invention claimed is:

1. A medical dressing having a first side and a second opposing side, the first side comprises an adhesive layer having a skin-facing surface adapted to detachably adhere the medical dressing to a dermal surface, the medical dressing further comprising a first tag,
   wherein the first tag holds identifiable information that is readable, using an electronic device, wherein the identifiable information of the first tag is only readable if a predetermined portion of the skin-facing surface is detached from the dermal surface such that the first tag is visibly observable.

2. The medical dressing according to claim 1, wherein the predetermined portion of the skin-facing surface is visibly observable only if at least 25% of the adhesive layer is detached from the dermal surface.

3. The medical dressing according to claim 1, wherein the predetermined portion of the skin-facing surface is visibly observable only if at least 40% of the adhesive layer is detached from the dermal surface.

4. The medical dressing according to claim 1, wherein the identifiable information of the first tag is optically readable using the electronic device.

5. The medical dressing according to claim 4, wherein the first tag is at least one of a one-dimensional (1D) and a two-dimensional (2D) bar code.

6. The medical dressing according to claim 1, wherein the first tag is adapted to employ radio frequency (RF) communication.

7. The medical dressing according to claim 6, wherein the first tag is at least one of a radio-frequency identification (RFID) tag and a near field communication (NFC) tag.

8. The medical dressing according claim 1, wherein the first tag is attachable to the medical dressing.

9. The medical dressing according to claim 1, further comprising at least one gripping tab, wherein the gripping tab is arranged coplanar with and projecting outwardly from a periphery of the medical dressing.

10. A medical dressing arrangement, comprising:
   a medical dressing according to claim 1; and
   an electronic device comprising means for reading identifiable information of the first tag.

11. The medical dressing arrangement according to claim 10, wherein the electronic device is a mobile electronic device.

12. The medical dressing arrangement according to claim 10, wherein the electronic device comprises a graphical user interface (GUI) adapted to provide a user with an instruction to read the identifiable information of the first tag.

13. The medical dressing arrangement according to claim 12, wherein the electronic device further comprises a camera adapted to capture an image of at least a portion of the dermal surface in conjunction with reading of the first tag.

14. A medical dressing system, comprising:
   a medical dressing arrangement according to claim 11; and
   a server arranged in communication with the electronic device, wherein the server is adapted for storage of the identifiable information of with the tag and a time/date of reading the identifiable information.

15. A method for reading a first tag holding identifiable information, wherein the first tag is comprised with a medical dressing, the medical dressing having a first side and a second opposing side, the first side comprises an adhesive layer having a skin-facing surface adapted to detachably adhere the medical dressing to a dermal surface, wherein the method comprises:
   receiving, at an electronic device, a request to read the identifiable information of the first tag; and
   reading, using the electronic device, the identifiable information of the first tag, wherein the identifiable information is readable only if a predetermined portion of the skin-facing surface is detached from the dermal surface such that the first tag is visibly observable.

16. The method according to claim 15, wherein the electronic device is arranged in communication with a server and the method further comprises:
   determining a time/date of reading the identifiable information of the first tag; and
   storing the time/date and data related to the identifiable information of the first tag at a computer memory comprised with the server.

17. The method according to claim 15, further comprising:
   receiving an image of a portion of the dermal surface, wherein the image is captured in conjunction with reading the identifiable information of the first tag; and
   storing the image within the computer memory, wherein image is stored with a relation to the identifiable information of the first tag.

18. The method according to claim 15, further comprising:

detaching the predetermined portion of the skin-facing surface from the dermal surface.

* * * * *